United States Patent
Didon

(10) Patent No.: US 9,308,383 B2
(45) Date of Patent: Apr. 12, 2016

(54) METHOD, APPARATUS AND COMPUTER PROGRAM FOR DEFIBRILLATION DELIVERY DECISION

(75) Inventor: Jean-Philippe Didon, Merkwiller-Pechelbronn (FR)

(73) Assignee: SCHILLER MEDICAL S.A.S., Wissembourg (FR)

( * ) Notice: Subject to any disclaimer, the term of this patent is extended or adjusted under 35 U.S.C. 154(b) by 939 days.

(21) Appl. No.: 12/722,704

(22) Filed: Mar. 12, 2010

(65) Prior Publication Data
US 2011/0224746 A1 Sep. 15, 2011

(51) Int. Cl.
*A61N 1/39* (2006.01)
*A61B 5/00* (2006.01)

(52) U.S. Cl.
CPC .............. *A61N 1/39* (2013.01); *A61B 5/7207* (2013.01); *A61N 1/3925* (2013.01); *A61N 1/3987* (2013.01)

(58) Field of Classification Search
CPC .............. A61B 5/0428; A61B 5/7207; A61B 5/04017; A61N 1/39; A61N 1/3925; A61N 1/3987
USPC .................. 607/5, 6, 9, 50; 600/500, 509, 513
See application file for complete search history.

(56) References Cited

U.S. PATENT DOCUMENTS

| | | | |
|---|---|---|---|
| 6,553,257 B2 | 4/2003 | Snyder et al. | |
| 6,807,442 B1 * | 10/2004 | Myklebust et al. | 600/509 |
| 8,509,881 B2 * | 8/2013 | Thiagarajan et al. | 600/509 |
| 2002/0133197 A1 | 9/2002 | Snyder et al. | |
| 2004/0162585 A1 * | 8/2004 | Elghazzawi et al. | 607/5 |
| 2006/0116724 A1 * | 6/2006 | Snyder | 607/5 |
| 2006/0173501 A1 * | 8/2006 | Stickney et al. | 607/5 |
| 2007/0060785 A1 * | 3/2007 | Freeman et al. | 600/16 |

FOREIGN PATENT DOCUMENTS

DE 69114517 10/1996

OTHER PUBLICATIONS

Jekova et al., "Real time detection of ventricular fibrillation and tachycardia", Physiol. Meas. 25, 1167-1178, Centre of Biomedical Engineering, Bulgarian Academy of Sciences, IOP Publishing Ltd, 2004.
Ruiz de Gauna et al., "A method to remove CPR artefacts from human ECG using only the recorded ECG", Elsevier Resuscitation 76, 271-278, Elsevier Ireland Ltd., 2007.
Aramendi et al., "Detection of ventricular fibrillation in the presence of cardiopulmonary resuscitation artefacts", Elsevier Resuscitation 72, 115-123, Elsevier Ireland Ltd., 2006.

* cited by examiner

*Primary Examiner* — Christopher D Koharski
*Assistant Examiner* — Pamela M Bays
(74) *Attorney, Agent, or Firm* — Davis & Bujold PLLC; Michael J. Bujold

(57) ABSTRACT

A method, apparatus and computer program for defibrillation delivery decision comprising the steps of: a) Determining a shockable rhythm with a first algorithm, whereby said first algorithm is adapted to analyze an ECG signal in the presence of chest compression; b) Determining a shockable rhythm with a second algorithm, whereby said second algorithm is adapted to analyze an ECG in the absence of chest compression; c) Determining with a third algorithm if the patient is undergoing chest compression.

4 Claims, 3 Drawing Sheets

METHOD, APPARATUS AND COMPUTER PROGRAM FOR DEFIBRILLATION DELIVERY DECISION

The present invention relates to a method for defibrillation delivery decision, an apparatus and a computer program product according to the preamble of the independent claims.

BACKGROUND

Sudden Cardiac Arrest (SCA) is one of the major reasons of death in industrialised countries. The condition is characterized by life-threatening abnormal rhythms of the heart, so called arrhythmia. Common arrhythmia includes Ventricular Fibrillation (VF) or Ventricular Tachycardia (VT)—a quivering of the heart that impairs its function of pumping blood to the body and brain. The patient loses its pulse, eventually consciousness and finally breathing ability. All these symptoms can occur in a matter of seconds. Life support and rescue needs to be fast.

In supporting the rescue of patients, Automated External Defibrillators (AED) play a major role. An effective treatment is the delivery of an electrical shock to defibrillate the heart. For this to be successful, it is necessary to recognise the presence and indication for a shockable rhythm. To keep the reduced blood flow in the meantime from damaging the patient's organs and brains, Cardio Pulmonary Resuscitation or Reanimation (CPR) is applied. Also, some type of arrhythmia can be treated by the first respondent with CPR alone, while waiting or the emergency team.

An essential feature of AED is thus the capability to detect shockable rhythms. The VF detection algorithms have to advise to shock with an accuracy of more than 90% (sensitivity) and advise not to shock with an accuracy of more than 95% (specificity). For AED that are to be used in the public, eventually by untrained personnel, it is thus critical that safety for the patient and rescuer is warranted. The American Heart Association has set forth recommendation for Specifying and Reporting Arrhythmia Analysis Algorithms Performance (AHA Scientific Statement, Kerber, R. E. et. al., Circulation Vol. 95, No 6, Mar. 18, 1997).

The benchmarks above are defined on the basis of non noisy signals. The main kind of noise that could impair the analysis process, are artefacts generated by the chest compression on the thorax of the patient. These artefacts are highly non-reproducible from patient to patient or from rescuer to rescuer. The pattern might even change for a specific rescuer over time.

Detection of a shockable rhythm is done by analysing the patient's Electrocardiogram (ECG). The ECG reproduces the activity of a patient's heart by graphically displaying the electrical activity of the heart. AED commonly use sophisticated algorithms for analysing the patient's heart rhythm and devising the therapy, e.g. indicating the presence of a shockable rhythm. One common problem is the presence of artefact signals that can result from various sources, the most prominent being the performance of CPR upon the patient. Artefacts can also result from patient motion during transport, the rescuer unintentionally touching the electrode pads, the patient's electrode—skin contact and many other sources.

The state of the art suggests varying ways for addressing the problem of artefacts. The presence of artefacts could lead to a wrong diagnosis. Thus, U.S. 2006/0025825 discloses a way to minimize the risk of a wrong diagnosis because of artefacts. For this end transthoracic impedance is measured separately from ECG. Based on the presence or absence of transthoracic impedance variations it is decided whether to shock, not to shock or to halt ECG measurement as a whole. Transthoracic impedance measurement has long since been suggested as flanking method for reliability surveillance of ECG. It has been sought to increase specificity by using transthoracic impedance as indication of bloodflow, or heamodynamics (Johnston, P. W. et al, The transthoracic impedance cardiogram is a potential heamodynamic sensor for an automated external defibrillator, European Heart Journal (1998) 19, 1876-188).

There are also possibilities of compensating the artefacts during CPR. U.S. Pat. No. 6,287,328 shows a method of enhancing the detection and taking into account of artefact signals. Artefact reference signals (so called "non-event signals") are measured along so called "event signals" (ECG signals) and correlated by multi-variable artefact assessment. Presence and significance of artefacts from multiple potential sources are detected along a cardiac event signal. This additional information is used to support the decision whether the signal of interest (for example ECG signals) is to be trusted and can be used for defibrillation shock decision.

A further way of minimizing signal disturbances during CPR is disclosed in U.S. Pat. No. 6,807,442. A measurement of the compression and/or inflation of the chest is correlated with the signal disturbance (eq. artefact). A filter is used to eliminate said disturbances. The algorithm can thus conclude while CPR still being performed, reducing the time used for shock delivery and allowing more time for CPR.

In the attempt of minimizing the time for reaching a decision to deliver a shock, U.S. 2007/0213775 A1 (included herein by reference) teaches a defibrillator with minimal delay following the CPR intervals. The delay is minimized by quickly discriminating the end of a CPR period.

U.S. 2006/0129190 A1 also suggests a method for rapidly delivering a defibrillation shock, if indicated, by determining a probability, based on a first set of signals for presence of a shockable rhythm. A precharging is initiated, if the probability is high enough and then, a second set of data determines whether the therapy can be delivered. This earlier charging should reduce the time lag caused by the capacitor having to charge.

All the prior art solution are insufficient though, as they do not duly consider the required sensitivity and specificity benchmarks when using artefact compensation, or require too much time for finding a shockable rhythm if they do not use an artefact compensation. If the time the ECG needs to find a shockable rhythm is essentially 'hands-off' time with no CPR being performed, there are detrimental effects for the patient. Survival rates are highest, when defibrillation is conducted within the first few minutes after onset of arrhythmia and "hands off" time is minimised.

SUMMARY OF THE INVENTION

It is an object of the present invention to provide a solution to the problems of the state of the art. In particular a rapid and safe defibrillation delivery system should be provided. Even more particularly, the present invention provides a system for significantly reducing the time interval from cessation of CPR until defibrillation delivery decision is reached. The present invention also provides a rapid defibrillation delivery decision system in the presence of artefacts.

The problem is solved with a method for defibrillation delivery decision, an apparatus and a computer program product according to the characterizing portion of the independent patent claims.

One aspect of the present invention is a method for defibrillation delivery decision, including the steps of determining if the patient has a shockable rhythm with a first algorithm. Said first algorithm is adapted to analyze an ECG signal for shockable rhythms in the presence of chest compression. The method further includes determining if a patient has a shockable rhythm with a second algorithm. Said second algorithm is adapted to analyze an ECG in the absence of chest compression. With a third algorithm it is determined if the patient is under-going chest compression.

A shockable rhythm is defined as an ECG analysis output that advises the use of a defibrillator shock or a sequence defibrillator shocks to restore heart functionality.

Following initial diagnosis of SCA, healthcare professionals further categorise the diagnosis based on the ECG rhythm. Among the rhythms which result in a cardiac arrest, there is Ventricular fibrillation (VF) and pulseless ventricular tachycardia (VT), both responsive to a defibrillator, and so, colloquially referred to as "shockable" rhythms, whereas asystole and pulseless electrical activity (PEA) are examples for non-shockable rhythms. The nature of the presenting heart rhythm suggests different causes and treatment, and is used to guide the rescuer as to what treatment may be appropriate. Knowledge of whether delivery of a defibrillation shock is the proper indication is growing, further identifying previously as non-shockable classified rhythms as shockable and vice versa with gradually being able to distinguish sub-patterns. The present invention is thus not limited to VF and/or pulseless VT, but can, as is evident to the skilled artisan, be adapted to incorporate the latest scientific state of the art with routine procedures. Also, is possible to distinguish between shockable and non shockable VF.

The delivered shock can be a single shock or a sequence of shocks (1-Shock Protocol or 3-Shock Sequence for example). Modern defibrillators are equipped to provide the lowest effective energy to terminate VF/VT. Several types of waveforms can be used in context with the invention: monophasic, biphasic with fixed or escalating energy, triphasic, quadriphasic etc. For the present invention the skilled artisan can easily choose the implementation, which best fits the purposed application of the intended device. A discussion on electrical therapies is supplied herein by reference of the Journal 'Circulation' published by the American Heart Association (Part 5: Electrical Therapies: Automated External Defibrillators, Defibrillation, Cardioversion, and Pacing; Circulation 2005; 112; IV-35-IV-46; November 2005).

In a preferred embodiment of the invention, the determining whether the patient has a shockable rhythm is performed with ventricular fibrillation and/or ventricular tachycardia detection.

In a preferred embodiment of the invention, the third algorithm is based on transthoracic impedance measurement.

In a preferred embodiment of the invention, a beginning and/or end of chest compression is detected with the third algorithm.

During CPR the patient's chest is compressed with physical force by the rescuer. This results in a change in transthoracic impedance. Impedance measurement can thus be used to determine whether chest compression is present or not. It has been found, that the detection of shockable rhythms can be performed with increased reliability (specifity and sensitivity) and more rapidly by using algorithms that are capable of determining shockable rhythms in the presence of chest compression combined with algorithms that are capable of determining shockable rhythms in the absence of chest compression. As both of these algorithms only perform reliably if their environmental conditions are met (e.g. chest compression is present or absent), the third algorithm crucially determines the presence or absence of chest compression.

Once the end of chest compression is detected by the third algorithm, the much more reliable second algorithm takes over for detection of shockable rhythms.

In a preferred embodiment the time interval between actual cessation of chest compression and detection of cessation is retroactively analysed with the second algorithm.

As chest compressions are timed executions on the patients' body that can vary slightly in cadence depending on rescuer and protocol. It is impossible to immediately determine the end of chest compression with the third algorithm at the same time the last stroke is performed. There is a time interval between the actual end of chest compression (the rescuer takes his, hands off the patient and stops performing compressions) and the detected end of chest compression (the third algorithm notices that variations in transthoracic impedance are sufficiently low to decide that chest compression must have stopped).

This data gathered and analysed with the first algorithm during this time interval between cessation of CPR and detection of cessation of CPR may be retroactively analysed with the second algorithm.

The result gives the second algorithm significant lead time when analysing the ECG for shockable rhythms in the absence of chest compression, thus greatly enhancing the capability of rapidly detecting a reliable (high specificity and sensitivity) shockable rhythm.

In a preferred embodiment of the invention, the detection of cessation of CPR leads to a replacement of the first algorithm by the second algorithm, preferably taking into account retroactively analysed data.

In a preferred embodiment of the invention, the time interval for retroactive analysis covers less than ten seconds time after actual cessation of chest compression. In a more preferred embodiment, the time interval covers less than about 5 seconds of time after actual cessation of chest compression. In an attempt to reduce the "hands off" time, the delay between actual cessation and defection of cessation may be further reduced. Then, the time interval for retroactive analysis covers equal or less than three seconds of time after actual cessation of chest compression. The time intervals are preferably as small as possible and possibly close to or actually zero.

The time during which no CPR is performed should be kept as short as possible, as lack of circulation can lead to significant damage in organs and the brain of the victim.

In a preferred embodiment of the invention, at least two algorithms are performed in parallel to each other.

Another aspect of the invention is a method for defibrillation delivery decision, wherein a defibrillation shock delivery decision on the basis of a first algorithm is complemented with a second algorithm. Said first algorithm is adapted to analyze an ECG signal for shockable rhythms in the presence of chest compression. Said second algorithm is adapted to analyze an ECG signal in the absence of chest compression. The method preferably includes a third algorithm for determining if the patient is under-going chest compression.

In the sense of the present invention the first algorithm is used to consider during the second algorithm results provided by the first algorithm in a way that can be explained as complementation of algorithms. The data collected during the chest compression on the rhythms is thus complemented with the data collected in the absence of chest compression. This, paired with the retroactive analysis of the time interval detailed above, gives the second algorithm a considerable lead time in detecting the presence of a shockable rhythm thus increasing the reliability (specificity and sensitivity) of shockable rhythm detection.

A further aspect of the present invention is an apparatus for delivery of a defibrillation shock, with at least one ECG signal detection unit. The apparatus further has a chest compression measurement unit; a defibrillation shock delivery unit, and a processor. Said processor is capable of determining whether the patient has a shockable rhythm with a first algorithm. Said first algorithm is adapted to analyze an ECG signal for shockable rhythms in the presence of chest compression. The processor is further capable of determining whether a patient has a shockable rhythm with a second algorithm. Said second algorithm is adapted to analyze an ECG signal in the absence of chest compression.

In a further embodiment of the present invention, said processor is further capable of analysing signal input of the chest compression measurement unit.

In a further embodiment of the present invention, said processor is able to determine the beginning and/or end of chest compression based on the input of the chest compression measurement unit.

In a further embodiment of the present invention, the processor is able to identify the beginning and/or end of chest compression by analysing data from the chest compression measurement unit.

A further aspect of the present invention is a computer program product. The computer program product performs the following operations when it is run on a computer: determining whether a patient has a shockable rhythm with analysis of a first algorithm, determining whether a patient has a shockable rhythm with analysis of a second algorithm. Said first algorithm is adapted to analyze an ECG signal for shockable rhythms in the presence of chest compression. Said second algorithm is adapted to analyze an ECG in the absence of chest compression. With analysis of a third algorithm, the processor determines if the patient is undergoing chest compression.

BRIEF DESCRIPTION OF THE DRAWINGS

The invention will be further outlined in the following: in reference to the preferred embodiments with examples and drawings.

DETAILED DESCRIPTION OF THE PREFERRED EMBODIMENT

Figure 1:
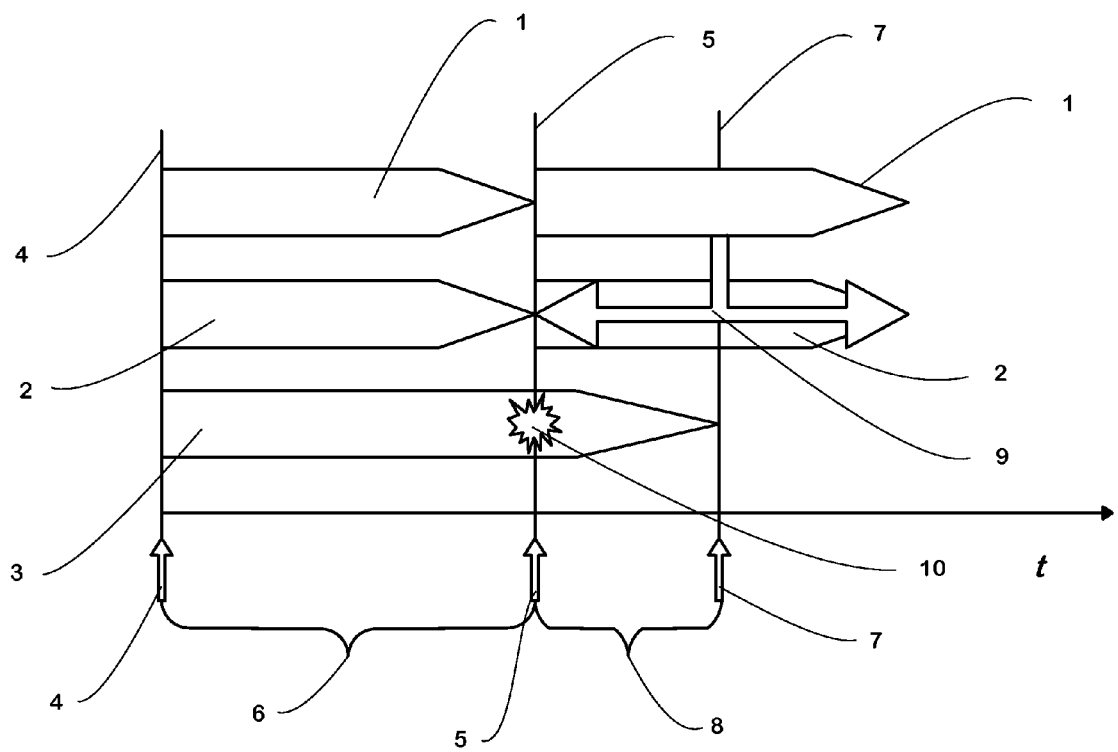
FIG. 1 shows a timeline of a SCA treatment with an AED in respect to the algorithms that are performed by the AED according to the invention.
Figure 2:
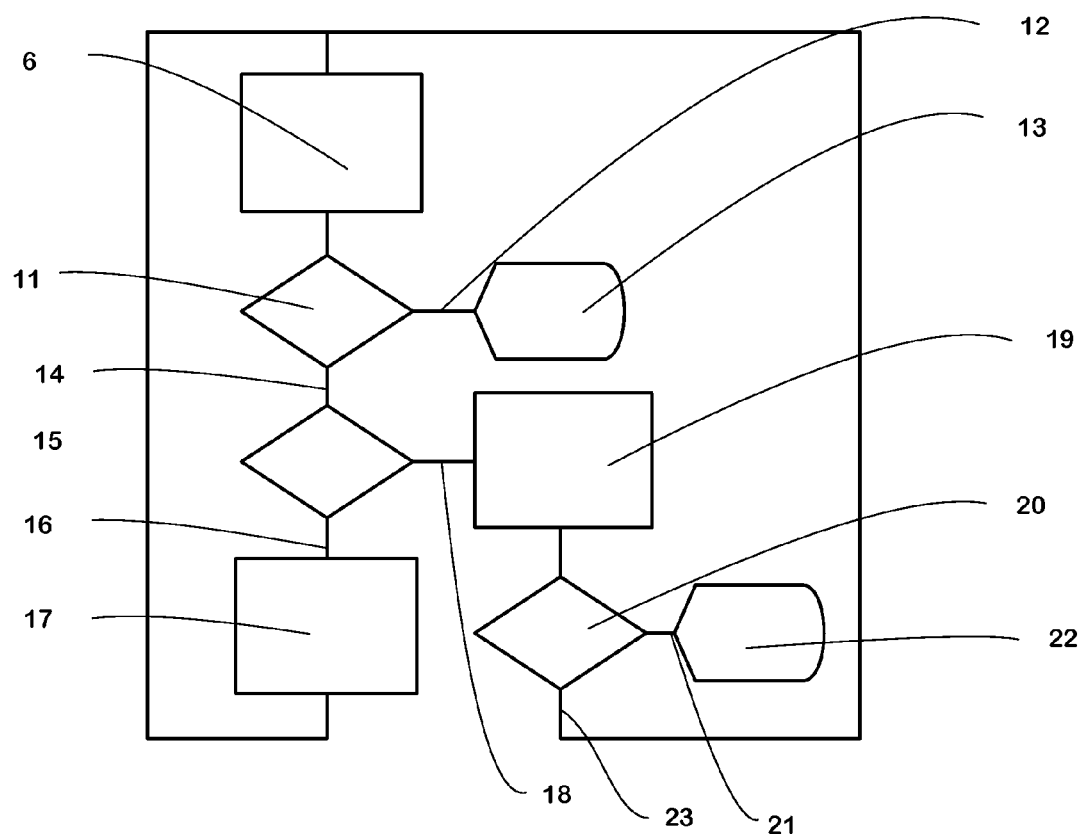
FIG. 2 shows a flowchart depicting the defibrillation delivery decision according to the present invention.

FIG. 1 and FIG. 2 illustrate the procedure of the present invention. In FIG. 1 the time axis t shows the reliance on the three algorithms 1, 2 & 3 for defibrillation delivery decision. A first detection algorithm 1—specialised in finding shockable rhythms in presence of chest compression—is run from start of CPR 4 for the time 6 while CPR is being performed. A second detection algorithm 2—specialised in finding shockable rhythms in the absence of chest compression—can also be run from the start of CPR 4, but becomes relevant for defibrillation delivery decision only once a detected end of CPR 7 has been detected by a chest compression analysis algorithm 3. The analysis for shockable rhythms proceeds with the algorithm 2, retroactively treating the data collected during the interval 8 between actual cessation of chest compression 5 and detection of end of chest compression 7 with algorithm 3. Furthermore, information provided by the first algorithm 1 during the CPR time 6 is considered 9 in the second algorithm 2. During the whole time axis t, a defibrillation delivery decision may be advised, depending on the analysis by the algorithms and the specific threshold for confidence level set through the sensitivity and specificity requirements. If a shockable rhythm has not been identified before the time point 10 in which the rescuer interrupts chest compression, the data from the analysis may be further used in the second algorithm 2 that replaces the first algorithm 1 for determining the presence of a shockable rhythm.

The VF detection algorithm 1 works during the whole chest compression period, about 1 minute and 30 seconds. After the end of the chest compression period the analysis algorithm reports to the main processor of the device if a shockable rhythm is present. If not, the CPR period is extended for X seconds. If a shockable rhythm is present, a prompt requiring the rescuer to stop chest compression is broadcasted.

The chest compression presence is monitored with the Chest compression detection algorithm, and during that time, ECG and impedance signals are recorded. The chest compression detection algorithm usually detects the end of compression in less than three seconds (e.g. the maximum expected time interval between two chest compressions).

A retroactive analysis of all data till the actual end of chest compression by the VF detection algorithm 2 (i.e. about 3 seconds of ECG without artefact) allows to complement the decision process begun by the VF detector 1. The final decision is more accurate and reliable.

For defibrillation delivery decision FIG. 2 shows a schematic pathway. While a first detection algorithm—specialised in finding shockable rhythms in presence of chest compression—runs during the time 6 CPR is performed, it is determined whether a shockable rhythm is present with a confidence level depending on sensitivity/specificity (YES/NO) 11, in the case it is (YES) 12, a defibrillation delivery advice is issued 13. In the case no shockable rhythm has been detected so far with the required confidence level (NO) 14, procedure runs with algorithm 1 if chest compression is found to be present (YES) 16. If at any time during the procedure the chest compression is found not to be present (NO) 18 by the chest compression detection (YES/NO) 15, the second algorithm 2 is used—specialised in finding shockable rhythms in the absence of chest compression. During this time 19, no chest compressions are performed. Said second algorithm 2 screens for shockable rhythm (YES/NO) 20 in the absence of chest compression. In case a shockable rhythm is found (YES) 21, a defibrillation delivery advice is issued 22. In case no such rhythm is detected (NO) 23, CPR can be resumed 17 and the procedure reiterated from the start. Of course, the system can also give a definite NO decision on the presence of shockable rhythm in the case the patient is considered clinically dead.

The rhythm detector process is composed of 2 VF detection algorithms and one chest compression analysis algorithm.

The first VF detection algorithm is adapted in finding the shockable rhythms under presence of chest compression. By principle it does not work properly on an ECG without CPR artefacts. Typically, VF detection algorithms specialised in finding shockable rhythms under presence of chest compression are quite sophisticated. Rheinberger, K. et al. describe a removal of artefacts based on the Kalman Method (Removal of Resuscitation Artefacts from Ventricular Fibrillation ECG Signals Using Kalman Methods; Rheinberger, K. et al.; Computers in Cardiology 2005; 32:555-558). Another suggestion is described by Klotz, A. et al. with the use of local coherent line removal (Removal of CPR Artefact in Ventricular Fibrillation ECG by Local Coherent Line Removal; Klotz, A. et al.; USIPCO. Conference No 12, (Jun. 9, 2004), [Note(s) : XXXV-2310] (14 ref.)).

For the present invention the method proposed by Aramendi, E. et al. (Detection of ventricular fibrillation in the presence of cardiopulmonary resuscitation artefacts; Aramendi, E. et al.; Resuscitation, 2007, Vol. 72, 115-123) can e.g. be used as the first algorithm. Alternatively a preprocessing can be applied to the ECG data. After such a preprocessing, any kind of VF detection algorithm can be applied. An example of such a preprocessing is shown in Ruiz de Gauna et al. (A method to remove CPR artefacts from human ECG using only the recorded ECG; Ruiz de Gauna, S. et al.; Resuscitation, 2008, Vol. 76, pages 271-278).

The second VF detection algorithm is specialised in finding the shockable rhythms in the absence of chest compression. The accuracy of this algorithm is known and higher than required by the AHA guidelines. It works on 1 second slices, but a 10 seconds period is currently necessary for good results. Such algorithms are well known in the art. A VF/VT detection method suitable for the second algorithm is e.g. shown in Jekova and Krasteva (Jekova, I. and Krasteva, V.; Real time detection of ventricular fibrillation and tachycardia; Physiological Measurement, 2004, Vol. 25, pages 1167-1178).

Parameters relevant for a potential shock decision are know in the art, like for example heart rate (HR), the number of signal samples around the zero line (Z), the number of signal samples near the saturation borders (M) etc. A method for processing an ECG signal for determination of the heart condition can be applied according to WO 9210805 A1. The statistic evaluation of the parameters are attributed with a specific type of signal (shockable/non shockable). In case of a shockable rhythm the parameters would be HR=HRs, Z=Zs, M=Ms ("s" for shockable). In case of a non shockable rhythm the parameters will have the following attributes HR=HRn, Z=Zn, M=Mn. These parameters are computed on a given duration of a signal, for example 2 second slices. After a certain number of intervals (for example 10 seconds, e.g. 5 slices), the sum of each parameter is performed and a test on the global value (in the above example on 10 seconds) allows to decide whether the rhythm is shockable or not.

In the present example, the parameters used by algorithm 1 are used to generate a vector from 1 to N values of the parameters (HR, Z, M) depending on the shape of the analysed signal. The vector is then used by algorithm 2 as if these were previously computed values.

The chest compression analysis algorithm is e.g. based on transthoracic Impedance variation measurements. This algorithm allows detecting the chest compression periods during rescue intervention.

The final charge of the capacitor is checked and a prompt requiring the rescuer to back up for shock is broadcasted during this last part of analysis (with VF Detector 2).

Based on two VF detection algorithms and on a chest compression detector, the current process/algorithms allow to analyse the status of the patient during chest compressions and to deliver the shock within a very short while after chest compression stopped. This algorithm limits drastically the 'hands-off' time, which is known to be related to patient outcome.

Current protocol to treat SCA includes the use of AED combined with periods of CPR. CPR is composed of two rescue gestures: applications of 30 Chest Compressions (CC) followed by two rescue breaths (RB). CPR protocols are constantly changing and being updated, reflecting the newest findings of the technical field. Alternatively, the use of newer rescue protocols is also applicable with the present invention. For example Cardio Cerebral Reanimation (CCR) can be used in conjunction with the present invention. As with CPR, CCR provides alternately chest compressions and possible shocks. The difference from CPR is that no more rescue breaths are delivered to the patient and 200 chest compressions are performed by the rescuers instead of 3 minutes of CPR. The analysis period is very short, because the charge of the capacitor is performed during the last chest compressions and the analysis is performed visually by the paramedics on the screen of the defibrillator monitor.

Figure 3:
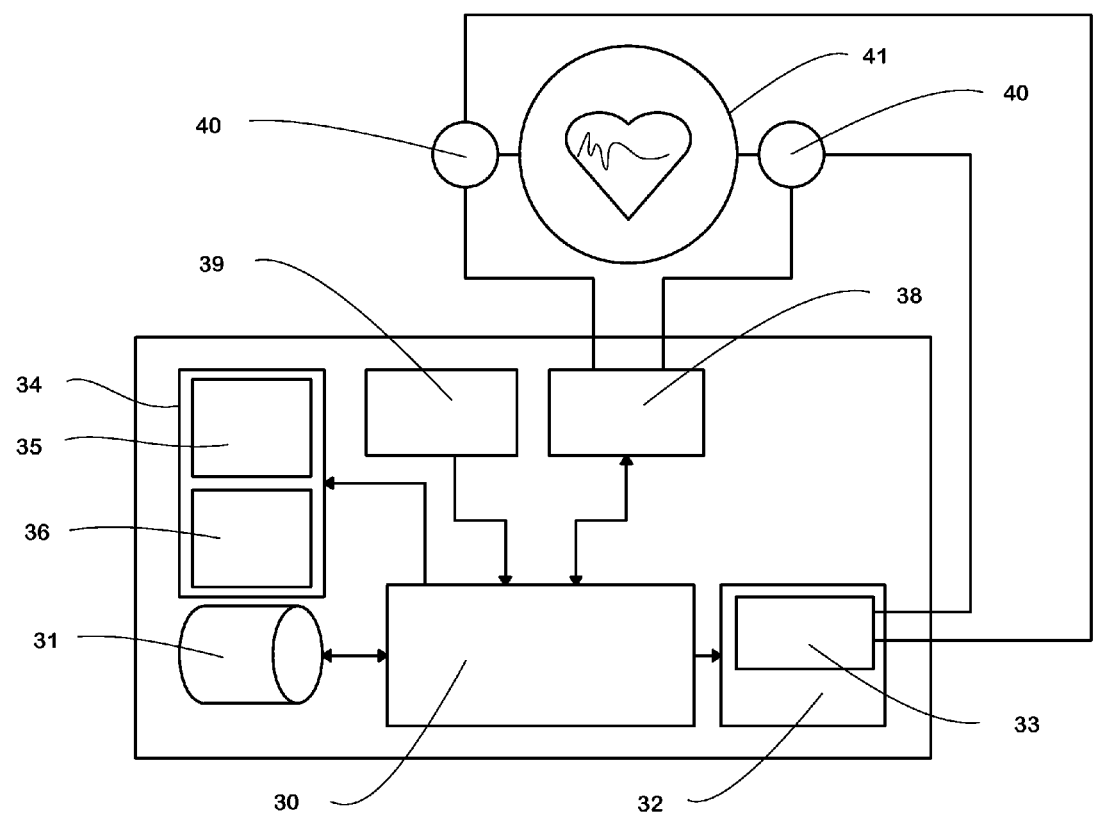
FIG. 3 shows a schematic standard defibrillator set-up according to the invention.

An example defibrillator or AED set up is shown in FIG. 3. An AED generally comprises an energy source 32 the circuitry for generating the defibrillation shock 33, such as a capacitor. An output unit 34 is further included, comprising an optical output monitor 35 and a voice prompt 36. The defibrillator further includes an ECG sensing circuit 38. Detection elements, such as electrode pads 40 are attached thereto. The user can interact with the machine through a user interface 39. During operation, a processor 30 is responsible for steering the various components according to the protocol and user input. The processor is further capable of storing data or retrieving data from a data storage unit 31. During operation, the electrode pads 40 are attached to the patient's thorax 41 and function as sensors and shock delivery elements in the same time.

For example FRED® easy defibrillators by Schiller Medical S.A.S (Wissembourg, FR) can be adapted by the person skilled in the art for exercising the present invention.

I claim:

1. Apparatus for delivery of a defibrillation shock, wherein said apparatus comprises:
   at least one ECG signal detection unit,
   a chest compression measurement unit,
   a defibrillation shock delivery unit, and
   a processor,
   wherein said processor is configured to determine whether the patient has a shockable rhythm with a first algorithm and said first algorithm is adapted to analyze an ECU signal for shockable rhythms in the presence of artifacts generated by chest compression and wherein said first algorithm only performs reliably if a chest compression is present and wherein said processor is further configured to determine whether a patient has a shockable rhythm with a second algorithm and said second algorithm is adapted to analyze an ECG signal in the absence of chest compression and wherein the second algorithm only performs reliably if to chest compression is absent,
   said processor is able to identify a starting point and an end point of chest compression by analysing data from the chest compression measurement unit with a third algorithm and
   said processor is configured to switch to the first algorithm when the starting point of chest compression is identified and to switch to the second algorithm when the end point of chest compression is identified by said processor.

2. The apparatus of claim 1, wherein said processor is further capable of analysing signal input of the chest compression measurement unit.

3. The apparatus of claim 1, wherein the processor identifies the beginning and/or the end of chest compression by analysing data from the chest compression measurement unit.

4. The apparatus of claim 1, wherein said processor is further capable of retroactively analysing data collected with the first algorithm with data from the second algorithm for the time interval between detection of cessation of CPR and actual cessation of CPR.

\* \* \* \* \*